United States Patent [19]

Kaji

[11] Patent Number: 5,639,728
[45] Date of Patent: Jun. 17, 1997

[54] ANTINEOPLASTIC PEPTIDE

[76] Inventor: Akira Kaji, 1-9, Daimoncho 1-chome, Higashikurume-shi, Tokyo, 203, Japan

[21] Appl. No.: 446,848

[22] PCT Filed: Sep. 30, 1994

[86] PCT No.: PCT/JP94/01632

§ 371 Date: Jun. 1, 1995

§ 102(e) Date: Jun. 1, 1995

[87] PCT Pub. No.: WO95/09871

PCT Pub. Date: Apr. 13, 1995

[30] Foreign Application Priority Data

Oct. 1, 1993 [JP] Japan .................................. 5-277269

[51] Int. Cl.⁶ ............................ C07K 1/00; C07K 14/00; C07K 17/00
[52] U.S. Cl. .................................. 514/12; 530/351
[58] Field of Search ........................... 530/351; 514/12

[56] References Cited

FOREIGN PATENT DOCUMENTS

| | | |
|---|---|---|
| 60-185799 | 9/1985 | Japan . |
| 63-8398 | 1/1988 | Japan . |
| 63-8399 | 1/1988 | Japan . |
| 63-270698 | 11/1988 | Japan . |
| 1-6298 | 1/1989 | Japan . |
| 1-29399 | 1/1989 | Japan . |
| 3-184994 | 8/1991 | Japan . |
| 4-45789 | 2/1992 | Japan . |
| 6-41196 | 2/1994 | Japan . |

OTHER PUBLICATIONS

Biotechnology vol. 7, Apr. 1989, pp. 363–368.

*Primary Examiner*—Frederick Krass
*Attorney, Agent, or Firm*—Birch, Stewart, Kolasch & Birch, LLP

[57] ABSTRACT

The present invention offers a novel polypeptide wherein 10 amino acids are deleted from the N-terminal of a native-form lymphotoxin and to this deletion site is added R-Phe-Pro-(R is Met or H). This novel polypeptide has high antitumor activity, little toxicity, does not display the hypotensive effect (lethal effect of lymphotoxins), and can be used as an active ingredient of a superior antitumor agent.

2 Claims, 1 Drawing Sheet

ANTINEOPLASTIC PEPTIDE

FIELD OF THE INVENTION

The present invention relates to a novel antineoplastic peptide.

BACKGROUND ART

Previously known antineoplastic peptides include TNF and lymphotoxin. TNF is problematic in that hypotension is a side effect and application in actual therapies is currently limited; likewise, lymphotoxin also has a hypotensive effect, and manufacture of recombinant lymphotoxin has drawbacks. Thus, at present, the research on lymphotoxin is not progressing well.

Heretofore, there have been various reports regarding derivatives comprising modified native-form lymphotoxin peptides. Examples include JP, A, S63-8398, JP, A, S63-8399, JP, A, S63-270698, JP, A, S64-6298, JP, A, S64-29399, JP, A, H3-184994, and JP, A, H4-45789.

However, such previously reported lymphotoxin derivatives (hereinafter referred to "LT derivatives") exhibit a hypotensive effect similar to that seen in TNF, and thus, in this respect, there is a problem to be solved.

As a result of extensive research involving various investigations on conventional LT derivatives, by means of the present invention, the present inventor succeeded in offering a novel peptide possessing an excellent antineoplastic effect.

DISCLOSURE OF THE INVENTION

The present invention offers a novel peptide possessing the amino acid sequence described by the following formula (I) (Provided, R indicates Met or H.).

R—Phe—Pro—Ala—Gln—Thr—Ala—Arg—Gln—His (I)
Pro—Lys—Met—His—Leu—Ala—His—Ser—Thr—Leu
Lys—Pro—Ala—Ala—His—Leu—Ile—Gly—Asp—Pro
Ser—Lys—Gln—Asn—Ser—Leu—Leu—Trp—Arg—Ala
Asn—Thr—Asp—Arg—Ala—Phe—Leu—Gln—Asp—Gly
Phe—Ser—Leu—Ser—Asn—Asn—Ser—Leu—Leu—Val
Pro—Thr—Ser—Gly—Ile—Tyr—Phe—Val—Tyr—Ser
Gln—Val—Val—Phe—Ser—Gly—Lys—Ala—Tyr—Ser
Pro—Lys—Ala—Thr—Ser—Ser—Pro—Leu—Tyr—Leu
Ala—His—Glu—Val—Gln—Leu—Phe—Ser—Ser—Gln
Tyr—Pro—Phe—His—Val—Pro—Leu—Leu—Ser—Ser
Gln—Lys—Met—Val—Tyr—Pro—Gly—Leu—Gln—Glu
Pro—Trp—Leu—His—Ser—Met—Tyr—His—Gly—Ala
Ala—Phe—Gln—Leu—Thr—Gln—Gly—Asp—Gln—Leu
Ser—Thr—His—Thr—Asp—Gly—Ile—Pro—His—Leu
Val—Leu—Ser—Pro—Ser—Thr—Val—Phe—Phe—Gly
Ala—Phe—Ala—Leu

The present invention also concerns usage in an antitumor agent containing such a peptide as an active ingredient.

The novel peptide pertaining to the present invention shows no hypotensive effect at an effective quantity showing antitumor activity, and in terms of antitumor activity, said peptide is also known to manifest the exceptional value of the chemotherapeutic index, seven times that of TNF. Consequently, the novel peptide pertaining to the present invention is extremely useful from the standpoint that it can be used in a drug serving as an antitumor agent.

The novel antineoplastic peptide pertaining to the present invention is obtained by expressing the peptide by means of DNA prepared by incorporating the modified LT gene into an expression vector. The modified LT gene was prepared as follows. Starting from a native-form human lymphotoxin (LT) gene, the DNA of a 10 amino acid segment (30 bases) has been removed from the N-terminal end segment of this DNA sequence, and DNA corresponding to Met, Phe, Pro or Phe, Pro amino acid sequence has been added. This peptide, namely, a peptide wherein the above-noted Phe and Pro amino acid sequence has been incorporated, is hereinafter denoted by "FPΔ10LT."

Specifically, the above-mentioned DNA can be assembled through the procedures shown in FIG. 1, for example. Through the method shown in FIG. 1, a vector expressing the peptide pertaining to the present invention can be assembled by cutting out a base sequence which codes the ribosome binding site (segment SD domain (gene 1)) and a base sequence which codes most of an LT structural gene (gene 2) from a well-known modified LT vector discussed hereafter, and ligating said sequences with a base sequence synthesized so as to include an initiator codon and an amino acid sequence (synthesis gene) and a vector (gene 3).

The modified LT vector (hereinafter referred to "pBtrp MLT") used in the procedures shown in FIG. 1 is essentially that developed by Seow et al. (Biotechnology 7, 363 [1989]) and somewhat modified by Morita et al. (JP, A, H4-45789). The use of this vector allows advantageous expression of lymphotoxins. This vector can be assembled by using a promoter in which the −10 region base sequence is TTAACT and the −35 region base sequence is TTGACA, establishing 13 bases between the SD domain (ribosome binding site) and the initiator codon (ATG). The lymphotoxin gene was then ligated to this DNA. The length of the vector DNA was 2.7–3.1 kb.

By using a modified LT vector obtained in the aforementioned manner to genetically transform a host microorganism according to a routine method, then culturing the genetically transformed microorganism, the desired peptide can be produced.

Culturing of the genetic transformant can also be performed according to a routine method, i.e. L-agar, M9-agar, M9-casamino acid agar, high phosphate concentration culture medium, and high phosphate concentration casamino acid culture medium or the like can be used.

If particularly high expression is desired, addition of 3β-indoleacrylic acid to the culture medium is favorable. The added amount of 3β-indoleacrylic acid is approximately 20 to 100 μg per 1 ml culture medium.

The desired peptide obtained by culturing may be separated from the culture medium and purified by a method such as pulverizing the microorganisms by ultrasonic treatment and obtaining a supernatant by centrifuging. This supernatant may then be purified by a combination of purification techniques such as ammonium sulfate precipitation, dialysis, hydrophobic chromatography, or affinity chromatography.

Working examples and experimental examples are offered next and describe the present invention in further detail, but the present invention is in no way restricted by these working examples.

WORKING EXAMPLE 1

Assembly and Expression of FPΔ10LT Gene (1) Collection of the trp promoter segment and the LT structural gene from pBtrp MLT vector BamH I (Toyobo) and Cla I (Pharmacia) restriction endonucleases were brought to reaction with pBtrp MLT DNA, and after low melting point agarose gel electrophoresis, a trp promoter segment comprising 127 bp (gene 1) was collected. Additionally, Nsi I (NEB) and Hind III (Toyobo) restriction endonucleases were brought to reaction with pBtrp MLT DNA, and after low melting point agarose gel electrophoresis, a 456 bp LT structural gene (gene 2) was collected.

3

(2) Assembly of LT End Segment

A gene coding an LT end segment (synthetic gene) was similarly prepared from the four oligonucleotides 1) through 4) shown below, while maintaining a 13 base separation between the SD domain and the initiator codon.
1) 5' CGA TAA GCT ATG TTT CCA GCC CAG
2) 3' T ATT CGA TAC AAA GGT CGG GTC TGA CGG
3) 5' ACT GCC CGT CAG CAC CCC AAG ATG CA
4) 3' GCA GTC GTG GGG TTC T 0.2 OD each of oligonucleotides 2) and 3) of the above-noted oligonucleotides was dissolved in 15 µl sterilized water, and T4 polynucleotide kinase (Toyobo), 1 µl 10 mM ATP, 3 µl kination buffer solution (600 mM Tris-HCl, pH 8.0; 100 mM MgCl$_2$; 150 mM β-mercaptoethanol), and water were added to form a total volume of 30 µl which was brought to reaction at 37° C. for 2 hours. After the reaction, a 10 minute heat treatment at 65° C. was performed, and the enzymes were deactivated.

Thereafter, 0.05 OD each of oligonucleotides 1) through 4) were brought together in a single tube, subjected to 10 minute heat treatment at 90° C. in a 40 µl reaction mixture containing 25 mM Tris-HCl (pH 7.5) and 5 mM MgCl$_2$, and slowly cooled.

The following were added thereto, forming a 50 µl volume: 2000 units T4 DNA ligase (Toyobo), 0.5 µl 1M DTT, 5 µl 10 mM ATP, 5 µl annealing buffer solution (500 mM Tris-HCl, pH 7.6; 100 mM MgCl$_2$), and 7.5 µl water. The reaction was then carried out for 16 hours at 16° C., the material was subjected to 20% polyacrylamide gel electrophoresis and EtBr staining, the target gene was cut out, eluted in an eluting buffer solution (0.5M ammonium acetate, 1 mM EDTA), and desalted. The synthesis gene obtained had the following base sequence.

4 genetic transformant possessing pBtrp FPΔ10LT was obtained. DNA was separated from this genetic transformant, cleaved by BamH I—Hind III restriction endonucleases, subjected to 1% agarose gel electrophoresis and EtBr staining, and confirmed to be a 635 bp fragment.

(5) pBtrp FPΔ10LT Expression

Protein expression with regard to pBtrp FPΔ10LT obtained in the foregoing (4) was checked at 37° C. A single colony of pBtrp FPΔ10LT was inoculated into 10 ml M9CA/Hepes culture medium (M9 minimal medium, 0.5% glucose, 1 mM MgSO$_4$, 0.1 mM CaCl$_2$, 0.5% casamino acid, 0.1 mg/ml thiamine hydrochloride, 0.05 mg/ml ampicillin, and 100 mM Hepes) containing 100 µg/ml tryptophan and incubated overnight at 30° C. The following day, 1/50 of the amount was inoculated into 10 ml of fresh M9CA/Hepes culture medium and cultured until OD$_{550}$=0.5. 3β-indoleacrylic acid was then added to obtain final concentration of 20 µg/ml. The culture temperature was then changed to 37° C., and the bacteria were cultured for 16 hours.

After culturing was complete, 1 ml microbial solution was transferred to a 1.5 ml centrifuge tube, and the microbes were obtained by centrifugation. The microbes were dissolved in 200 µl SDS-PAGE buffer solution, heat treated for 5 minutes at 95° C., and electrophoresed in 15% SDS-PAGE. After electrophoresis, the protein was stained with Coomassie blue and the gel was destained. The amount of FPΔ10LT expressed per total protein measured by a Pharmacia laser scanner was found to be 10% of the total protein under the culturing conditions at 37° C. This corresponds to a 10 to 20 mg protein quantity per 1 l at 37° C.

(6) Production and Purification of FPΔ10LT

E. coli HB101 possessing pBtrp FPΔ10LT was cultured overnight in 200 ml M9CA/Hepes culture medium contain-

| Synthetic gene | | | | | | | | |
|---|---|---|---|---|---|---|---|---|
| | | | Met | Phe | Pro | Ala | Gln | Thr |
| CGA | TAA | GCT | ATG | TTT | CCA | GCC | CAG | ACT |
| T | ATT | CGA | TAC | AAA | GGT | CGG | GTC | TGA |
| Ala | Arg | Gln | His | Pro | Lys | Met | | |
| GCC | CGT | CAG | CAC | CCC | AAG | ATG | CA | |
| CGG | GCA | GTC | GTG | GGG | TTC | T | | |

(3) Blue Script SK II (+) Cleavage

2 µg of Blue Script SK II (+) (Toyobo) were cleaved by BamH I—Hind III restriction endonucleases and subjected to 0.8% low melting point agarose gel electrophoresis and EtBr staining, and plasmid DNA comprising the target 2.9 Kb (gene 3) was obtained.

(4) Assembly of plasmid containing FPΔ10LT gene possessing trp promoter

T4 DNA ligase was added to a mixture of genes 1, 2, 3 and the Synthetic gene 1, and a plasmid (pBtrp FPΔ10LT) containing the FPΔ10LT gene was obtained. E. coli HB 101 stock microbe for genetic transformation previously stored frozen at −70° C. was melted, and 20 µl (10 ng DNA) pBtrp FPΔ10LT was added to 100 µl (1.3×10$^8$ cells) of this suspension.

After 45 minutes ice cooling, a heat shock was applied for 90 seconds at 42° C., followed by a further 2 minutes ice cooling. 900 µl SOC culture medium (2% Bactotryptone, 0.5% yeast extract, 10 mM NaCl, 2.5 mM KCl, 10 mM MgCl$_2$, 10 mM MgSO$_4$, and 20 mM glucose) was added, and the material was cultured for 1 hour at 37° C. The suspension was then spread on an LB agar plate containing 0.1 mg/ml ampicillin, cultured overnight at 37° C., and a ing 100 µg/ml tryptophan, and 7 l M9CA/Hepes culture medium was inoculated with this culture solution and cultured at 30° C. until OD$_{550}$=0.5. Thereafter, 3β-indoleacrylic acid was added so as to comprise a final concentration of 20 µg/ml, the culturing temperature was again changed to 37° C., and the material was cultured 16 hours. After culturing, 17.81 g (wet) microbes were obtained by centrifuging. 8.83 g thereof was suspended in 250 ml 50 mM tris-hydrochloride (pH 8.0) containing 30 mM NaCl, 2 mM p-APMSF (protease inhibitor), and 1 mM EDTA; this microbial suspension was passed three times through a high pressure homogenizer (Rannie) at 6,000 psi, and the microbes were pulverized.

A supernatant free from microbial residue was obtained by further centrifuging.

Polyethylenimine was added to 272 ml of the supernatant obtained so as to comprise a final concentration of 0.075%, centrifuging was performed, and nucleic acid was removed. 268 ml of this supernatant was recovered, ammonium sulfate was added to form a 50% saturation, the material was agitated for 2 hours at 4° C., centrifuging was performed, and a crude protein was obtained as a precipitate.

This crude protein was dissolved in 70 ml 20 mM phosphate buffer solution (pH 7.0) and dialyzed overnight using the above buffer solution. Insoluble proteins formed overnight were removed by centrifuging the crude protein solution, and 77 ml of the supernatant fluid was recovered. This 77 ml recovered solution was adsorbed onto a CM sepharose fast flow column (Pharmacia) previously balanced with 20 mM phosphate buffer solution (pH 7.0), and was then washed with 20 mM phosphate buffer solution (pH 7.0) and eluted by a stepwise concentration gradient in a 20 mM phosphate buffer solution (pH 7.0) containing 0 to 1M NaCl (65 ml).

This eluate was concentrated by an Amicon ultrafiltering device (U-10), and a 17 ml concentrated solution was obtained. This concentrated solution was applied to a φ26× 600 mm Sephacryl S-200 (Pharmacia), a gel filtration carrier, which was thoroughly balanced with physiological saline in advance.

A peptide-containing fraction was collected from the eluate. Activity was determined by L-929 testing, and specific activity and yield were determined in various purification processes. Protein content was measured using a Biorad protein assay system, and 49.4 mg FPΔ10LT was obtained from the active fraction. These results are shown in Table 1.

units/ml, $5 \times 10^7$ units/mg), and this solution was administered intravenously to the mice twice per week; a total five times. In a control group, physiological saline alone was administered intravenously.

When 21 days following the transplant had passed, surviving animals were sacrificed, and tumors were excised. The excised tumors were weighed, and a mean tumor weight was calculated in each group. The mean tumor weight in each administration group was compared with the mean tumor weight in the control group, and tumor growth restriction rates were determined.

Based on the tumor growth restriction rates obtained at various concentrations, concentrations restricting tumor growth by 50% (50% effective dose; $ED_{50}$ mg/kg) were calculated. In each administration group, when toxicity deaths were observed, a 50% lethal quantity (50% lethal dose; $LD_{50}$ mg/kg) was calculated. The therapeutic index was taken as the ratio of the 50% lethal quantity ($LD_{50}$) to the 50% tumor growth restriction quantity ($ED_{50}$)

The tested substances used in this testing were the FPΔ10LT pertaining to the present invention prepared in Working Example 1, the MLT[1] disclosed in JP, A, H4-45789, and the PΔ10LT[2] and FΔ10LT[3] disclosed in JP, A, S63-270698. Control Δ10LT[4] was the TNF disclosed in JJP, A, S60-185799.

TABLE 1

| | Total volume of solution (ml) | Protein concentration (mg/ml) | Total protein content (mg) | LT activity (unit/ml) | Total activity (unit) | Specific activity (unit/mg) | Recovery (%) | Purification (fold) |
|---|---|---|---|---|---|---|---|---|
| Microbe pulverization solution | 272 | 5.9 | 1604 | $5.2 \times 10^7$ | $1.4 \times 10^{10}$ | $8.7 \times 10^6$ | 100 | 1 |
| 0.075% polyethylenimine treatment | 268 | 5.05 | 1353 | $4.5 \times 10^7$ | $1.2 \times 10^{10}$ | $8.8 \times 10^6$ | 85.7 | 1.01 |
| 50% Ammonium sulfate | 77 | 4 | 280 | $8.6 \times 10^7$ | $6.7 \times 10^9$ | $2.4 \times 10^7$ | 47.8 | 2.75 |
| CM-collection fraction | 65 | 1.68 | 109.2 | $9.5 \times 10^7$ | $6.2 \times 10^9$ | $5.7 \times 10^7$ | 44.2 | 6.55 |
| Gel filtration fraction | 38 | 1.3 | 49.4 | $9.9 \times 10^7$ | $3.8 \times 10^9$ | $7.5 \times 10^7$ | 27.1 | 8.74 |

(7) Purity assay of purified FPΔ10LT and determination of molecular weight and partial structure 2 µg of purified FPΔ10LT were electrophoresed by 15% SDS-PAGE, stained with Coomassie blue, decolored, and assayed for purity with a Pharmacia laser scanner. Results showed that this peptide was 95% or more pure.

The molecular weight of this peptide was found to be approximately 17,800 (theoretical value 18,771) by gel electrophoresis, and when the N-terminal amino acid sequence was analyzed by a gas phase protein sequencer (Applied Biosystems, Model 477A), said sequence of the peptide was found to be Met-Phe-Pro-Ala-Gln-Thr-Ala-Arg-Gln-His.

WORKING EXAMPLE 2

Study of Antitumor Effect

The following experiments were performed in order to calculate a therapeutic index (ratio of toxicity and effectiveness). $2 \times 10^5$ Meth A mouse sarcoma cells were transplanted into the dorsal subcutis of 6-week-old female Balb/c mice in single groups comprising from 5 to 10 animals. Seven days after the tumor transplant, the tested substance was dissolved in physiological saline ($9.9 \times 10^7$ Note [1]): MLT: Native-form lymphotoxin with 10 amino acid residues deleted from the N-terminal and 5 amino acid residues added at the deletion site.
[2]): PΔ10LT: Substance with a proline residue added at the above-mentioned deletion site.
[3]): FΔ10LT: Substance with a phenylalanine residue added at the aforementioned deletion site.
[4]): Δ10LT: Native-form lymphotoxin with 10 amino acid residues deleted from the N-terminal.

These results are shown in Table 2.

TABLE 2

| Tested substance | Dose (mg/kg) | Inhibition rate (%) | $ED_{50}$ (mg/kg) | $LD_{50}$ (mg/kg) | Treatment coefficient ($LD_{50}/ED_{50}$) |
|---|---|---|---|---|---|
| FPΔ10LT (Working Example) | 3.75 | 95.8 | 0.31 | 7.5 | 23.8 |
| | 0.94 | 78.9 | | | |
| | 0.23 | 49.8 | | | |
| | 0.06 | 20.5 | | | |
| MLT (Comparative Example) | 0.94 | 95.8 | 0.29 | 3.26 | 11.4 |
| | 0.23 | 39.8 | | | |
| | 0.06 | 12.1 | | | |
| PΔ10LT | 15.0 | 84.8 | 0.7 | >15.0 | >21.4 |

TABLE 2-continued

| Tested substance | Dose (mg/kg) | Inhibition rate (%) | ED$_{50}$ (mg/kg) | LD$_{50}$ (mg/kg) | Treatment coefficient (LD$_{50}$/ED$_{50}$) |
|---|---|---|---|---|---|
| (Comparative Example) | 3.75 | 72.5 | | | |
| | 0.94 | 51.4 | | | |
| | 0.23 | 19.6 | | | |
| FΔ10LT | 3.75 | 87.2 | 0.57 | 7.5 | 13.1 |
| (Comparative Example) | 0.94 | 70.5 | | | |
| | 0.23 | 14.9 | | | |
| Δ10LT | 15.0 | 84.2 | 0.46 | >15.0 | 32.9 |
| (Comparative Example) | 3.75 | 81.2 | | | |
| | 0.94 | 63.6 | | | |
| | 0.23 | 38.5 | | | |
| TNFα | 0.94 | 86.5 | 0.31 | 1.08 | 3.5 |
| (Comparative Example) | 0.23 | 43.3 | | | |

The above results show that the antitumor activity of the FPΔ10LT pertaining to the present invention against Meth A was equivalent to that of comparative items TNFα, MLT, and FΔ10LT, but the therapeutic index compared thereto was better by a factor from 2 to 7. The results also show that ED$_{50}$ was lower than that of comparative items PΔ10LT and Δ10LT.

EXPERIMENTAL EXAMPLE 1

Studies Regarding Blood Pressure

Using 11-week-old Crj:CD(SD) rats 350 to 400 g in weight (Nihon Charles River), effects of each test substance on blood pressure were investigated as follows. The aforementioned rats were given ether anesthesia, hair in the right femoral region was cue with clippers, and the skin was cut open using a small scissors. Xylocaine jelly (local anesthetic) was then applied to the cut skin, and each blood vessel was carefully peeled using a tweezers. After the peeling, an SP10 cannulation tube equipped with a three-way cock (Natsume) was attached to arteries and veins, and 200 unit/ml heparin solution was injected therefrom.

After insertion, the skin was sutured using an automatic stitcher, and the rats were secured to a stationary platform (Natsume, Boormann cage). After securing, air in the three-way cock of the arterial cannula was completely removed, and a polygraph (Nihon Denki Sanei, Model 363 System) pressure transducer was connected. After connection, the polygraph was set up, blood pressure measurement was begun, and when blood pressure and heart rate had stabilized, each tested substance used in the foregoing antitumor effect testing was administered by intravenous injection, and 24 hour systolic blood pressure was measured after administration.

After measurement began, flushing (heparin treatment) was also carried out one hour prior to each point to ensure that signals to the transducer would not be impaired by blood clots.

For each sample, 4 measurements were performed and dosages were intravenous administration at 1 mg/kg, 3 mg/kg, and 10 mg/kg. In data analysis, the bp at the time of the sample administration was taken as 100%, and a reduction in systolic blood pressure was indicated by subtraction. These results are shown in Table 3.

TABLE 3

Decrease of blood pressure (% of the control value) 24 hours after administration of cytokines to SD rats. The controls were given saline.

| Test substance | 1 mg/kg Dose | t-test | 3 mg/kg Dose | t-test | 10 mg/kg Dose | t-test |
|---|---|---|---|---|---|---|
| FPΔ10LT | +0.4% | — | −1.5% | — | +0.9% | — |
| MLT | +0.9% | — | −2.8% | — | +0.1% | — |
| PΔ10LT | −7.0% | * | untested | | untested | |
| FΔ10LT | −8.2% | * | untested | | untested | |
| Δ10LT | −6.8% | * | untested | | untested | |
| LT | −10.1% | * | untested | | untested | |
| TNFα | −9.6% | * | untested | | untested | |

*$P < 0.05$

With larger effective dosages of the FPΔ10LT pertaining to the present invention than the ED$_{50}$ value showing antitumor activity, the foregoing results show no hypotensive effect which is deemed as the most lethal side effect of lymphotoxins. In terms of therapeutic index, the results also show that all existing LT varieties display a significant hypotensive effect making them unfit for therapy, including PΔ10LT and Δ10LT displaying equivalent or better utility than the FPΔ10LT pertaining to the present invention.

EFFECT OF THE INVENTION

The novel peptide pertaining to the present invention has higher antitumor activity than previously reported recombinant-form lymphotoxins, recombinant-form lymphotoxin derivatives, and TNF, and side effects are also reduced. Consequently, the novel peptide pertaining to the present invention can be used advantageously as an antitumor agent or other drug.

Figure 1:
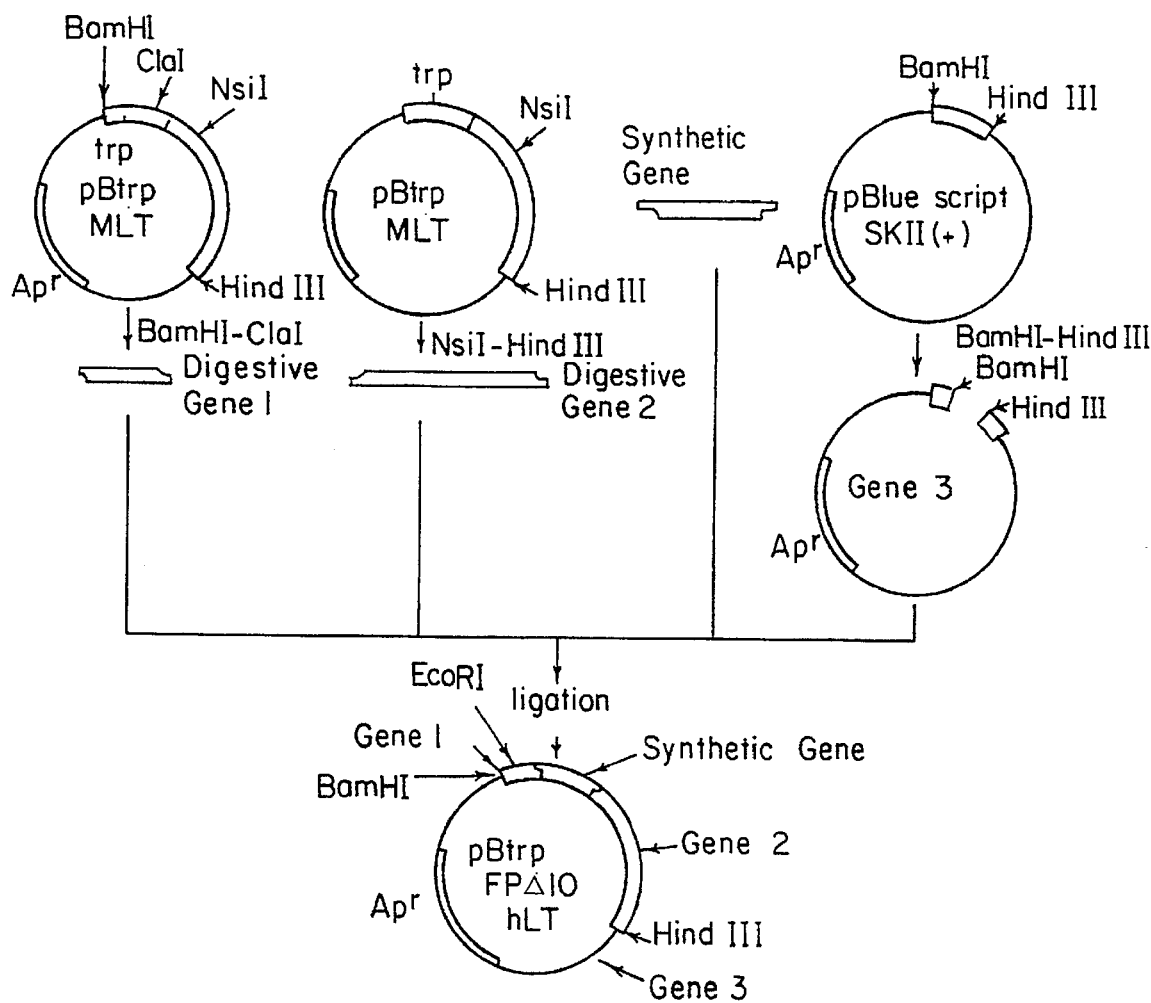
FIG. 1 is a drawing showing the assembly process for the plasmid producing the peptide pertaining to the present invention.

| Sequence Sheet | |
|---|---|
| Sequence number: | 1 |
| Sequence length: | 617 |
| Sequence form: | Nucleic acid |
| Number of strands: | Double-stranded |
| Topology: | Linear strand |
| Sequence type: | cDNA |
| Origin: | Human lymphocyte |

-continued

| Sequence characteristics | |
|---|---|
| Code describing characteristics: | −35 signal |
| Existing location: | 53..58 |
| Method for determining characteristics: | E |
| Sequence characteristics | |
| Code describing characteristics: | −10 signal |
| Existing location: | 76..81 |
| Method for determining characteristics: | E |

Sequence

```
                                                                AATTCATTGTC      11
CGACATCCAC AACGGTTCTGGC AAATATTCTG AAATGAGCTG TTGACAATTA ATCATCGAA              71
                                                   1
                                              Met .Phe .Pro⁻ .
CTAGTTAACT AGTACGC AAGTTCACGT AAAAAGGGT ATCGATAAGCT.ATG.TTT.CCA.                127

5                10                  15
Ala .Gln .Thr .Ala .Arg .Gln .His .Pro .Lys .Met .His .Leu .Ala .His .Ser .
GCC.CAG.ACT.GCC.CGT.CAC.CAT.CCC.AAG.ATG.CAT.CTT.GCC.CAC.AGC.                    172

20              25              30
Thr .Leu .Lys .Pro .Ala .Ala .His .Leu .Ile .Gly .Asp .Pro .Ser .Lys .Gln .
ACC.CTC.AAA.CCT.GCT.GCT.CAC.CTC.ATT.GGA.GAC.CCC.AGC.AAG.CAG.                    217

35              40              45
Asn .Ser .Leu .Leu .Trp .Arg .Ala .Asn .Thr .Asp .Arg .Ala .Phe .Leu .Gln .
AAC.TCA.CTG.CTC.TGG.AGA.GCA.AAC.ACG.GAC.CGT.GCC.TTC.CTC.CAG.                    262

50              55              60
Asp .Gly .Phe .Ser .Leu .Ser .Asn .Asn .Ser .Leu .Leu .Val .Pro .Thr .Ser .
GAT.GGT.TTC.TCC.TTG.AGC.AAC.AAT.TCT.CTC.CTG.GTC.CCC.ACC.AGT.                    307

65              70              75
Gly .Ile .Tyr .Phe .Val .Tyr .Ser .Gln .Val .Val .Phe .Ser .Gly .Lys .Ala .
GGC.ATC.TAC.TTC.GTC.TAC.TCC.CAG.GTG.GTC.TTC.TCT.GGG.AAA.GCC.                    352

80              85              90
Tyr .Ser .Pro .Lys .Ala .Thr .Ser .Ser .Pro .Leu .Tyr .Leu .Ala .His .Glu .
TAC.TCT.CCC.AAG.GCC.ACC.TCC.TCC.CCA.CTC.TAC.CTG.GCC.CAT.GAG.                    397

95             100              105
Val .Gln .Leu .Phe .Ser .Ser .Gln .Tyr .Pro .Phe .His .Val .Pro .Leu .Leu .
GTC.CAG.CTC.TTC.TCC.TCC.CAG.TAC.CCC.TTC.CAT.GTG.CCT.CTC.CTC.                    442

110             115              120
Ser .Ser .Gln .Lys .Met .Val .Tyr .Pro .Gly .Leu .Gln .Glu .Pro .Trp .Leu .
AGC.TCC.CAG.AAG.ATG.GTG.TAT.CCA.GGG.CTG.CAG.GAA.CCC.TGG.CTG.                    487

125             130              135
His .Ser .Met .Tyr .His .Gly .Ala .Ala .Phe .Gln .Leu .Thr .Gln .Gly .Asp .
CAC.TCG.ATG.TAC.CAC.GGG.GCT.GCG.TTC.CAG.CTC.ACC.CAG.GGA.GAC.                    532

140             145              150
Gln .Leu .Ser .Thr .His .Thr .Asp .Gly .Ile .Pro .His .Leu .Val .Leu .Ser .
CAG.CTA.TCC.ACC.CAC.ACA.GAT.GGC.ATC.CCC.CAC.CTA.GTC.CTC.AGC.                    577

155             160      164
Pro .Ser .Thr .Val .Phe .Phe .Gly .Ala .Phe .Ala .Leu .*** .***
CCT.AGT.ACT.GTC.TTC.TTT.GGA.GCC.TTC.GCT.CTG.TAG.TAG.A                           617
```

I claim:

1. A peptide which consists of the amino acid sequence described by the following formula (I), wherein R indicates Met or H:

R—Phe—Pro—Ala—Gln—Thr—Ala—Arg—Gln—His (I)
Pro—Lys—Met—His—Leu—Ala—His—Ser—Thr—Leu
Lys—Pro—Ala—Ala—His—Leu—Ile—Gly—Asp—Pro
Ser—Lys—Gln—Asn—Ser—Leu—Leu—Trp—Arg—Ala
Asn—Thr—Asp—Arg—Ala—Phe—Leu—Gln—Asp—Gly
Phe—Ser—Leu—Ser—Asn—Asn—Ser—Leu—Leu—Val
Pro—Thr—Ser—Gly—Ile—Tyr—Phe—Val—Tyr—Ser
Gln—Val—Val—Phe—Ser—Gly—Lys—Ala—Tyr—Ser
Pro—Lys—Ala—Thr—Ser—Ser—Pro—Leu—Tyr—Leu

Ala—His—Glu—Val—Gln—Leu—Phe—Ser—Ser—Gln
Tyr—Pro—Phe—His—Val—Pro—Leu—Leu—Ser—Ser
Gln—Lys—Met—Val—Tyr—Pro—Gly—Leu—Gln—Glu
Pro—Trp—Leu—His—Ser—Met—Tyr—His—Gly—Ala
Ala—Phe—Gln—Leu—Thr—Gln—Gly—Asp—Gln—Leu
Ser—Thr—His—Thr—Asp—Gly—Ile—Pro—His—Leu
Val—Leu—Ser—Pro—Ser—Thr—Val—Phe—Phe—Gly
Ala—Phe—Ala—Leu.

2. A method for treating tumors which comprises administering, to a mammal in need of such treatment an effective antitumor amount of a peptide according to claim 1.